(12) United States Patent
Brand et al.

(10) Patent No.: US 8,685,935 B2
(45) Date of Patent: Apr. 1, 2014

(54) USE OF FLAVONOIDS TO INCREASE THE BIOAVAILABILITY OF HESPERETIN

(75) Inventors: Walter Brand, Dg-wageningen (NL); Gary Williamson, Yorkshire (GB); Peter Van Bladeren, Corseaux (CH); Ivonne M. C. M. Rietjens, CW-Wageningen (NL)

(73) Assignee: Nestec S.A., Vevey (CH)

( * ) Notice: Subject to any disclaimer, the term of this patent is extended or adjusted under 35 U.S.C. 154(b) by 138 days.

(21) Appl. No.: 13/260,961

(22) PCT Filed: Mar. 30, 2010

(86) PCT No.: PCT/EP2010/054215
§ 371 (c)(1),
(2), (4) Date: Sep. 29, 2011

(87) PCT Pub. No.: WO2010/112510
PCT Pub. Date: Oct. 7, 2010

(65) Prior Publication Data
US 2012/0022010 A1 Jan. 26, 2012

(30) Foreign Application Priority Data
Mar. 31, 2009 (EP) .................................. 09156910

(51) Int. Cl.
*A61K 31/353* (2006.01)
(52) U.S. Cl.
USPC ........................................................ 514/27
(58) Field of Classification Search
USPC ........................................................ 514/27
See application file for complete search history.

(56) References Cited

U.S. PATENT DOCUMENTS 5,587,176 A    12/1996   Warren et al.

FOREIGN PATENT DOCUMENTS

JP          8283154      10/1996

OTHER PUBLICATIONS

Glossary of medical education terms, Institute of International Medical Education. http://www.iime.org/glossary.htm Accessed in Mar. 2013.*
Nijveldt et al. Flavonoids: a review of probable mechanisms of action and potential applications. Am J Clin Nutr 74:418-425, 2001.*
Youdim et al. Flavonoid Permeability Across an in Situ Model of the Blood-Brain Barrier. Free Rad Biol Med 36:592-604, 2004.*
Lyseng-Williamson et al., "Micronised purified flavonoid fraction: A review of its use in chronic venous insufficiency, venous ulcers and haemorrhoids," Drugs, vol. 63, Issue 1, 2003, pp. 71-100, XP009121133.
Zhang et al., "Combined effects of multiple flavonoids on breast cancer resistance protein (ABCG2)-mediated transport," Pharmaceutical Research (Dordrecht), vol. 21, Issue 7, Jul. 2004, pp. 1263-1273, XP002540809.
Zhang et al., "Structure activity relationships and quantitative structure activity relationships for the flavonoid-mediated inhibition of breast cancer resistance protein," Biochemical Pharmacology, Pergamon, Oxford, GB, vol. 70, Issue 4, Aug. 2005, pp. 627-639, XP004975979.
Brand et al., "Flavonoid-mediated inhibition of intestinal ABC transporters may affect the oral bioavailability of drugs, food-borne toxic compounds and bioactive ingredients," Biomedicine and Pharmacotherapy, Elsevier, vol. 60, Issue 9, Nov. 2006, pp. 508-519, XP025163495.
Brand et al., "Metabolism and transport of the citrus flavonoid hesperetin in Caco-2 cell monolayers," Drug Metabolism and Disposition, vol. 36, Issue 9, Sep. 2008, pp. 1794-1802, XP009121098.
PCT International Search Report for Application No. PCT/EP2010/054215 with a Mailing Date of May 17, 2010.
Written Opinion of the PCT International Searching Authority for Application No. PCT/EP2010/054215 with a Mailing Date of May 17, 2010.
Beneventa-Garcia, et al., "Update on Uses and Properties of Citrus Flavonoids: New Findings in Anticancer, Cardiovascular, and Anti-inflammatory Activity," J. Agric. Food Chem, 2008, vol. 56, Issue 15, pp. 6185-6205.
Galati et al., "Biological effects of hesperidin, a citrus flavonoid (Note I): Anti-inflammatory and analgesic activity", Farmaco, 1994, vol. 49, Issue 11, pp. 709-712.
Young Jin Moon, et al. "Dietary flavonoids: Effects on xenobiotic and carcinogen metabolism," Toxicology in Vitro, vol. 20, Issue 2, Mar. 2006, pp. 187-210.
Choi et al., "Evaluation of hesperitin 7-O-lauryl ether as lipid-lowering agent in high-cholesterol-fed rats", Bioorg. Med. Chem., Jul. 1, 2004, vol. 12, Issue 13, pp. 3599-3605.
Kaul et al., "Antiviral effect of flavonoids on human viruses," Journal of Medical Virology, Jan. 1985, vol. 15, Issue 1, pp. 71-79.
Miyagi et al., "Inhibition of Azoxymethane-Induced Colon Cancer by Orange Juice," Nutrition and Cancer, 2000, vol. 36, Issue 2, pp. 224-229.
Katayama et al., "Flavonoids inhibit breast cancer resistance protein-mediated drug resistance: transporter specificity and structure-activity relationship," Cancer Chemotherapy and Pharmacology Nov. 2007, vol. 60, Issue 6, pp. 789-797.
Zhang, et al., "Flavonoids Are Inhibitors of Breast Cancer Resistance Protein (ABCG2)-Mediated Transport," Molecular Pharmacology, May 2004, vol. 65, Issue 5, pp. 1208-1216.

(Continued)

*Primary Examiner* — Wu-Cheng Winston Shen
*Assistant Examiner* — Yih-Horng Shiao
(74) *Attorney, Agent, or Firm* — K&L Gates LLP

(57) ABSTRACT

The present invention relates generally to the field of hesperetin bioavailability. One embodiment of the present invention is directed at a composition that allows to increase the bioavailability of hesperetin and consequently to maximize the beneficial health effects of hesperetin.

9 Claims, 4 Drawing Sheets

(56) References Cited

OTHER PUBLICATIONS

Zhang, et al., Flavonoids Chrysin and Benzoflavone, Potent Breast Cancer Resistance Protein Inhibitors, Have no Significant Effect on Topotecan Pharmacokinetics in Rats or MDR1A (−/−) Mice, Drug Metabolism and Disposition, vol. 33, Issue 3, 2005, pp. 341-348.

Ahmed-Belkacem, et al., "Flavonoid Structure-Activity Studies Identify 6-Prenylchrysin and Tectochrysin as Potent and Specific Inhibitors of Breast Cancer Resistance Protein ABCG2," Cancer Res, 2005, vol. 65, Issue 11, pp. 4852-4860.

Cooray et al. "Interaction of the breast cancer resistance protein with plant polyphenols," Biochemical and Biophysical Research Communications, Apr. 2004, vol. 317, Issue 1, pp. 269-275.

Yoshikawa et al., "Transport of SN-38 by the wild type of human ABC transporter ABCG2 and its inhibition by quercetin, a natural flavonoid," Journal of Experimental Therapeutics & Oncology, 2004, vol. 4, Issue 1, pp. 25-35.

Wang, et al., "Effects of the flavonoid chrysin on nitrofurantoin pharmacokinetics in rats: potential involvement of ABCG2," Drug Metab. Dispos., 2007, vol. 35, Issue 2, pp. 268-274.

Henrich, et al., "A high-throughput cell-based assay for inhibitors of ABCG2 Activity," Journal of Biomolecular Screening, vol. 11, Issue 2, 2006, pp. 176-183.

Imai, et al., "Phytoestrogens/Flavonoids Reverse Breast Cancer Resistance Protein/ABCG2-Mediated Multidrug Resistance," Cancer Research, Jun. 2004, vol. 64, pp. 4346-4352.

* cited by examiner

USE OF FLAVONOIDS TO INCREASE THE BIOAVAILABILITY OF HESPERETIN

CROSS REFERENCE TO RELATED APPLICATIONS

The present application is a National Stage of International Application No. PCT/EP2010/054215, filed on Mar. 30, 2010, which claims priority to European Patent Application No. 09156910.3, filed on Mar. 31, 2009, the entire contents of which are being incorporated herein by reference.

The present invention relates generally to the field of hesperetin bioavailability. One embodiment of the present invention is directed at a composition that allows to increase the bioavailability of hesperetin and consequently to maximize the beneficial health effects of hesperetin.

Flavonoids (FIG. 1) consist of a large group of polyphenolic compounds which can be divided into different classes. They are present for example in fruits, vegetables and other plant-derived products. The flavanone (citrus flavonoid) hesperetin (FIG. 2) is the aglycone of hesperidin (hesperetin 7-O-rutinoside), which is the major flavonoid present in sweet oranges and orange juice. Hesperidin is also present in other citrus fruits including lemon, lime and mandarin, and can as well be found in several herbs such as mint (*Mentha piperita*). Hesperidin and hesperetin are reported to provide anti-inflammatory, anti-oxidant and anti-carcinogenic effects and to prevent bone loss. Depending on dietary habits, the amount of hesperidin can form an important part of the total flavonoid intake. However, according to data on the urinary and plasma concentrations, the bioavailability of hesperetin is limited due to efficient intestinal metabolism and efflux.

There is hence a need in the art to provide a sufficient amount of hesperetin to a subject.

It was consequently the object of the present invention to improve the state of the art and to provide a use and a composition to provide sufficient amounts of hesperetin to a subject, in particular to improve the bioavailability of hesperetin.

The inventors could achieve this object by the subject matter of the independent claims. The dependant claims further develop the present invention.

In particular, the inventors achieve this object by providing a composition and a use that allows hesperetin to become bioavailable to a higher extent and for longer periods of time.

This patent achieves this object by providing a novel method to increase the absorption of hesperetin and consequently to increase its bioavailability. The inventors demonstrate in vitro in a two-compartment cell culture model system simulating the intestinal barrier, that inhibition of BCRP, an ATP binding cassette (ABC) transporter at the apical (intestinal lumen) side, by co-administering inhibiting compounds, including other dietary flavonoids, results in a decreased efflux of metabolites of the citrus flavonoid hesperetin to the apical side, and in an increased efflux to the basolateral (blood/plasma) side.

These findings may be exploited to increase the bioavailability of hesperetin in vivo.

Flavonoids, as well as their metabolites, are substrates of ABC transporters which are present in the epithelial cells throughout the intestinal tract. In general, they are specifically located in the apical (intestinal lumen side) or basolateral (blood/plasma side) membrane of enterocytes and facilitate excretion back into the intestinal lumen or uptake into the blood stream, respectively. The most relevant intestinal ABC transporters include P-glycoprotein (Pgp), multidrug resistance protein 1 and 2 (MRP1 and MRP2) and breast cancer resistance protein (BCRP). Pgp, MRP2 and BCRP are localized in the apical membrane, whereas MRP1 is localized in the basolateral membrane.

The efficient intestinal metabolism and the efflux mediated by ABC transporters located in the apical membrane are believed to be the main reasons for the poor bioavailability of flavonoids and/or their metabolites.

Here it is demonstrated that flavonoids are inhibitors of ABC transporters present in the intestine, including BCRP. It is shown in vitro in a two-compartment model system with Caco-2 cell monolayers, a commonly used model simulating the intestinal barrier, that inhibition of BCRP results in a decreased efflux of the metabolites of the citrus flavonoid hesperetin to the apical (intestinal lumen) side, and in an increased efflux to the basolateral (blood/plasma) side.

Consequently, one embodiment of the present invention concerns the use of a composition comprising at least one flavonoid compound for the preparation of a product to provide an increased hesperetin ((S/R)-2,3-dihydro-5,7-dihydroxy-2-(3-hydroxy-4-methoxyphenyl)-4H-1-benzopyran-4-one) bioavailability in a mammal.

For example, one embodiment of the present invention concerns the use of a composition comprising at least one flavonoid compound with the proviso that the flavonoid is not hesperetin, for the preparation of a product to provide an increased hesperetin ((S/R)-2,3-dihydro-5,7-dihydroxy-2-(3-hydroxy-4-methoxyphenyl)-4H-1-benzopyran-4-one) bioavailability in a mammal.

Flavonoids are a class of plant secondary metabolites. According to the IUPAC nomenclature they can be classified into flavones which are derived from a 2-phenylchromen-4-one (2-phenyl-1,4-benzopyrone) structure; isoflavonoids, which are derived from a 3-phenylchromen-4-one (3-phenyl-1,4-benzopyrone) structure and neoflavonoids, which are derived from a 4-phenylcoumarine (4-phenyl-1,2-benzopyrone) structure.

Typical flavonoid compounds that can be used in the present invention may be selected from the group consisting of quercetin, fisetin, chrysin, acacetin, apigenin, luteolin tangeritin, baicalein, scutellarein, wogonin, diosmin and flavoxate, kaempferol, myricetin, fisetin, isorhamnetin, pachypodol, rhamnazin, hesperidin, rutin, galangin, kaempferide, genistein, daidzein, biochanin A, catechin, epicatechin, EGCG, phloretin, and combinations thereof.

The flavonoid compound may be selected from the group of compounds with the following general formula,

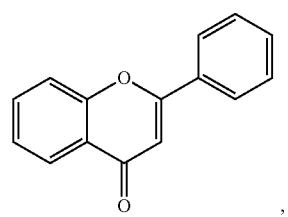

wherein carbons 3, 5, 6, 7, 8, 2', 3', 4', 5' and/or 6' are be substituted equally or different from one another with an H, OH, or OCH$_3$ group, with the proviso that the flavonoid compound is not hesperetin.

The carbons are numbered as shown in the molecule below:

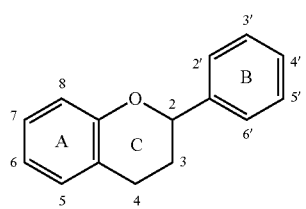

In one embodiment of the present invention it is preferred that the flavonoid compounds are dietary flavonoids.

A compound is considered as dietary if it is already present in foodstuff.

Good sources of dietary flavonoids include all citrus fruits, berries, *ginkgo biloba*, onions, parsley, pulses, tea, in particular white and green tea, red wine, seabuckthorn, and chocolate, preferably chocolate with a cocoa content of more than seventy percent.

The compounds mentioned above and/or the sources thereof may be used in the framework of the present invention. Flavonoid enriched fractions of these sources may be used as well.

The compounds of the present invention, e.g., the flavonoids, are administered in an amount sufficient to at least partially improve the hesperetin bioavailability and/or to reduce or arrest the symptoms of a disorder that can be treated or prevented by the administration of hesperetin. An amount adequate to accomplish this is defined as "a therapeutically effective dose". Amounts effective for this purpose will depend on a number of factors known to those of skill in the art such as the severity of the disease and/or the weight and general state of the patient. In prophylactic applications, compositions according to the invention are administered to a patient susceptible to or otherwise at risk of a particular disorder that can be treated or prevented by the administration of hesperetin in an amount that is sufficient to at least partially reduce the risk of developing a disease. Such an amount is defined to be "a prophylactic effective dose". Again, the precise amounts depend on a number of patient specific factors such as the patient's state of health and weight.

The compounds of the present invention are generally administered in a therapeutically effective dose and/or a prophylactic effective dose.

For example, the flavonoids may be administered in a daily dose in the range of 0.1 mg to 10000 mg, preferably 1 mg-1000 mg, more preferred 10 mg-500 mg.

The composition of the present invention can, but does not have to, contain hesperetin. It may be administered as such without any further addition of hesperetin. It will then be effective in increasing the bioavailability of hesperetin that is consumed with the normal food uptake or that is ingested and/or consumed in any other way.

Alternatively, the composition may also contain hesperitin. It may contain hesperitin in natural amounts or it may be enriched in hesperitin.

For example hesperetin may present in the composition and/or the product in a concentration that corresponds to a daily dose in the range of 0.01 mg to 10000 mg, preferably 1 mg-1000 mg, more preferred 10 mg-500 mg.

Hesperetin may be provided as pure compound, as hesperetin enriched extract or as normal foodstuff that contains hesperetin naturally. For example, hesperetin may be provided in the form of an extract from herbs such as mint or from citrus fruits, in particular from oranges, mandarins, lemons, limes, and/or grapefruits.

The product may be any product that can be used to administer the composition of the present invention to a subject.

For example, the product may be a food product, a pet food product, a nutraceutical, a food additive, a cosmetical composition or a medicament.

Food products include drinks and nutraceuticals, for example.

The composition may be intended for humans, pets or livestock.

Typically, the product of the present invention may be used to increase the effectiveness of hesperetin.

Hesperetin is for example known to increase the anti-oxidative defence of an organism as represented by numerous model systems (Beneventa-Garcia & Castillo, J Agric Food Chem. 2008; 56(15):6185-6205; document incorporated herein by reference).

Consequently, the product of the present invention may be used to increase the anti-oxidative defence of an organism. As such, the product of the present invention may be a cosmetical composition and may be intended to treat or prevent disorders related to ageing skin.

Hesperetin was also reported to be effective for sebum control and for the treatment of acne in mammalian skin and scalp (U.S. Pat. No. 5,587,176). Consequently, the product of the present invention may also be used for the prevention or treatment of acne, e.g., as a medicament or a cosmetical composition.

Hesperetin is further known to have an anti-inflammatory effect (Galati et al., Farmaco. 1994; 49(11):709-712; document incorporated herein by reference).

The product of the present invention may thus additionally or alternatively be used to treat or prevent inflammatory disorders. In particular it may be used to decrease the inflammatory level of a body.

Typical inflammatory disorders that can be treated or prevented by the product of the present invention may be selected from the group consisting of acute inflammations such as sepsis, infections, burns and chronic inflammations such as inflammatory bowel disease, Crohn's disease, ulcerative colitis, necrotizing enterocolitis, skin inflammation, such as UV or chemical-induced skin inflammation, eczema, reactive skin, psoriasis, vitiligo, inflammatory bowel syndrome, liver inflammation, alcoholic cirrhosis, allergy, atopy, bone inflammation, rheumatoid arthritis, systemic lupus, Gougerot-Sjögren's syndrome, Reiter's syndrome, poliomyelitis, dermato-myositis, thyroïditis, Basedow, Hashimoto, type I diabetes, Addison's disease, auto-immunes hepatitis, celiac disease, Biermer's disease, multiple sclerosis, myasthenia, encephalomyelitis, eye inflammation, obesity-associated inflammation, age-related low-grade inflammation, Blau's syndrome, cardiovascular diseases, atherosclerosis, metabolic syndrome, gingivitis and parondites.

In one embodiment of the present invention the product is a food product that may be used to treat or prevent inflammatory disorders.

In another embodiment of the present invention the product is a cosmetical composition that may be used to treat or prevent inflammatory disorders.

Hesperetin is further known to protect against toxins by inducing phase II enzymes as reported for other flavonoids (Young Jin Moon, Xiaodong Wang and Marilyn E. Morris Toxicology in Vitro Volume 20, Issue 2, March 2006, Pages 187-210; document incorporated herein by reference).

Hence, the product of the present invention may alternatively or additionally be used to protect a subject against toxins. Without wishing to be bound by theory, the inventors presently believe that this protective effect against toxins is achieved by an increase in the production of phase II enzymes. Phase II enzymes are the following (UDP-glucuronyltransferase, glutathione-S-transferase (GST), quinone reductase (QR) and sulfotransferases). Typical toxins that the product of the present inventions can protect against include electrophiles and/or compounds with electophilic reactive metabolites.

In one embodiment of the present invention the product is a food product that may be used to protect against toxins.

In another embodiment of the present invention the product is a cosmetical composition that may be used to protect against toxins.

Hesperetin is further known to prevent the formation of varicose veins, haemorrhoids, or venous ulcers (Lyseng-Williamson et al., Drugs. 2003; 63(1):71-100; document incorporated herein by reference).

The composition of the present invention may thus alternatively or additionally be used to treat or prevent the formation of varicose veins, haemorrhoids, or venous ulcers.

In one embodiment of the present invention the product is a cosmetical composition that may be used to treat or prevent the formation of varicose veins, haemorrhoids, or venous ulcers.

In another embodiment of the present invention the product is a medical composition that may be used to treat or prevent the formation of varicose veins, haemorrhoids, or venous ulcers.

Hesperetin is further known as a lipid lowering agent (Choi et al., Bioorg Med. Chem. 2004 Jul. 1; 12(13):3599-605, document incorporated herein by reference).

Hence, the product of the present invention may alternatively or additionally be used to treat or prevent high cholesterol levels, to increase HDL-cholesterol levels and/or to decrease levels of triglycerides in the blood. In this case the product of the present invention may be a food product, for example.

Hesperetin is further known to have an antiviral effect against human viruses (Kaul et al., J Med. Virol. 1985 January; 15(1):71-9, document incorporated herein by reference).

Hence, the product of the present invention may alternatively or additionally be used to treat or prevent viral infections, in particular herpes simplex type I and/or influenza infections.

In one embodiment of the present invention the product is a cosmetical composition that may be used to treat or prevent viral infections, in particular herpes simplex type I and/or influenza infections.

In another embodiment of the present invention the product is a medical composition that may be used to treat or prevent viral infections, in particular herpes simplex type I and/or influenza infections.

Hesperetin was also shown to reduce azoxymethane-induced colon cancer (Miyagi et al., Nutr Cancer. 2000; 36(2):224-9, document incorporated herein by reference).

Consequently, the product of the present invention may alternatively or additionally be used to treat, prevent or reduce cancer growth.

In one embodiment of the present invention the product is a medical composition that may be used to treat, prevent or reduce cancer growth.

In a further embodiment of the present invention the product is a food product that may be used to treat, prevent or reduce cancer growth.

A further embodiment of the present invention is a composition comprising
at least one flavonoid compound with the proviso that the flavonoid compound is not hesperetin, and
hesperetin,
wherein the at least one flavonoid compound and hesperetin are each present in an amount of 10 ng-10000 mg per daily dose.

The at least one flavonoid compound may be a compound with the following general formula,

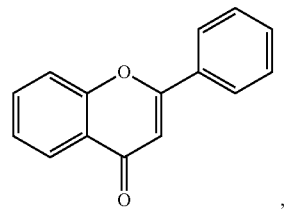

wherein carbons 3, 5, 6, 7, 8, 2', 3', 4', 5' and/or 6' are be substituted equally or different from one another with an H, OH, or OCH$_3$ group, with the proviso that the compound is not hesperetin.

It may also be selected from the group consisting of quercetin, fisetin, chrysin, acacetin, apigenin, luteolin tangeritin, baicalein, scutellarein, wogonin, diosmin and flavoxate, kaempferol, myricetin, fisetin, isorhamnetin, pachypodol, rhamnazin, hesperidin, rutin, galangin, kaempferide, genistein, daidzein, biochanin A, catechin, epicatechin, EGCG, phloretin, and combinations thereof.

For example, the composition of the present invention may contain hesperetin in an amount of at least 1000 mg/kg composition, for example at least 2000 mg/kg composition.

Additionally or alternatively, the composition of the present invention may contain the at least one flavonoid compound which is not hesperetin in an amount of at least 1000 mg/kg composition, for example at least 2000 mg/kg composition.

Those skilled in the art will understand that they can freely combine all features of the present invention described herein, without departing from the scope of the invention as disclosed. In particular, features described for the uses of the present invention may be applied to the composition and/or product of the present invention and vice versa.

Further advantages and features of the present invention are apparent from the following Examples and Figures.

Figure 1:
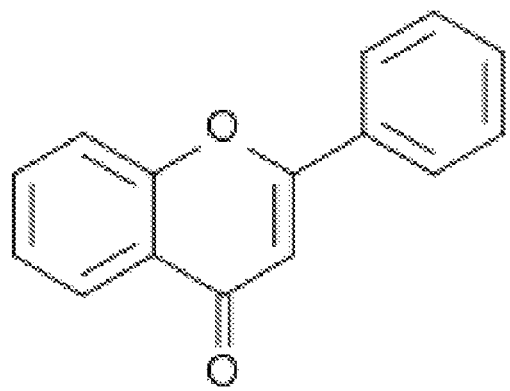
FIG. 1 shows the general chemical structure of flavonoids.
Figure 2:
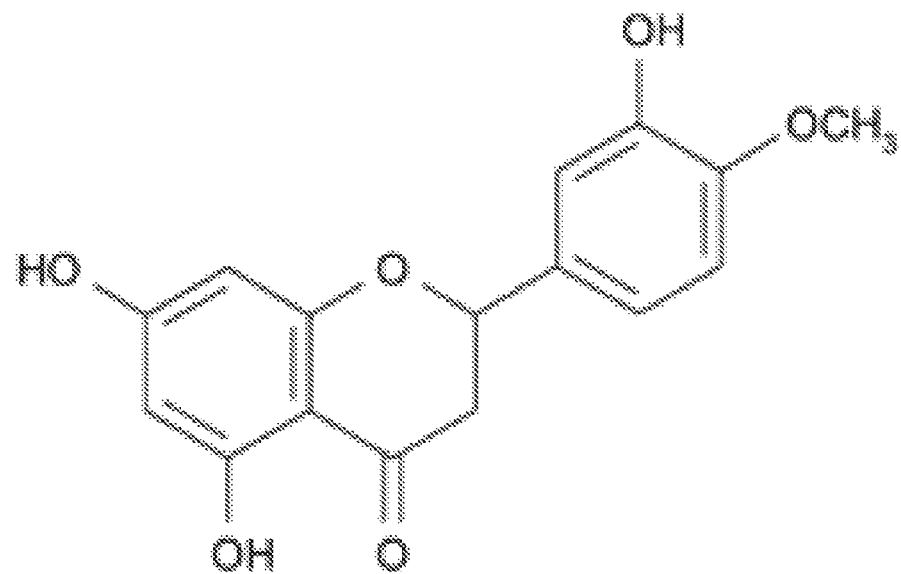
FIG. 2 shows the chemical structure of the flavanone (citrus flavonoid) hesperetin.
Figure 3A:
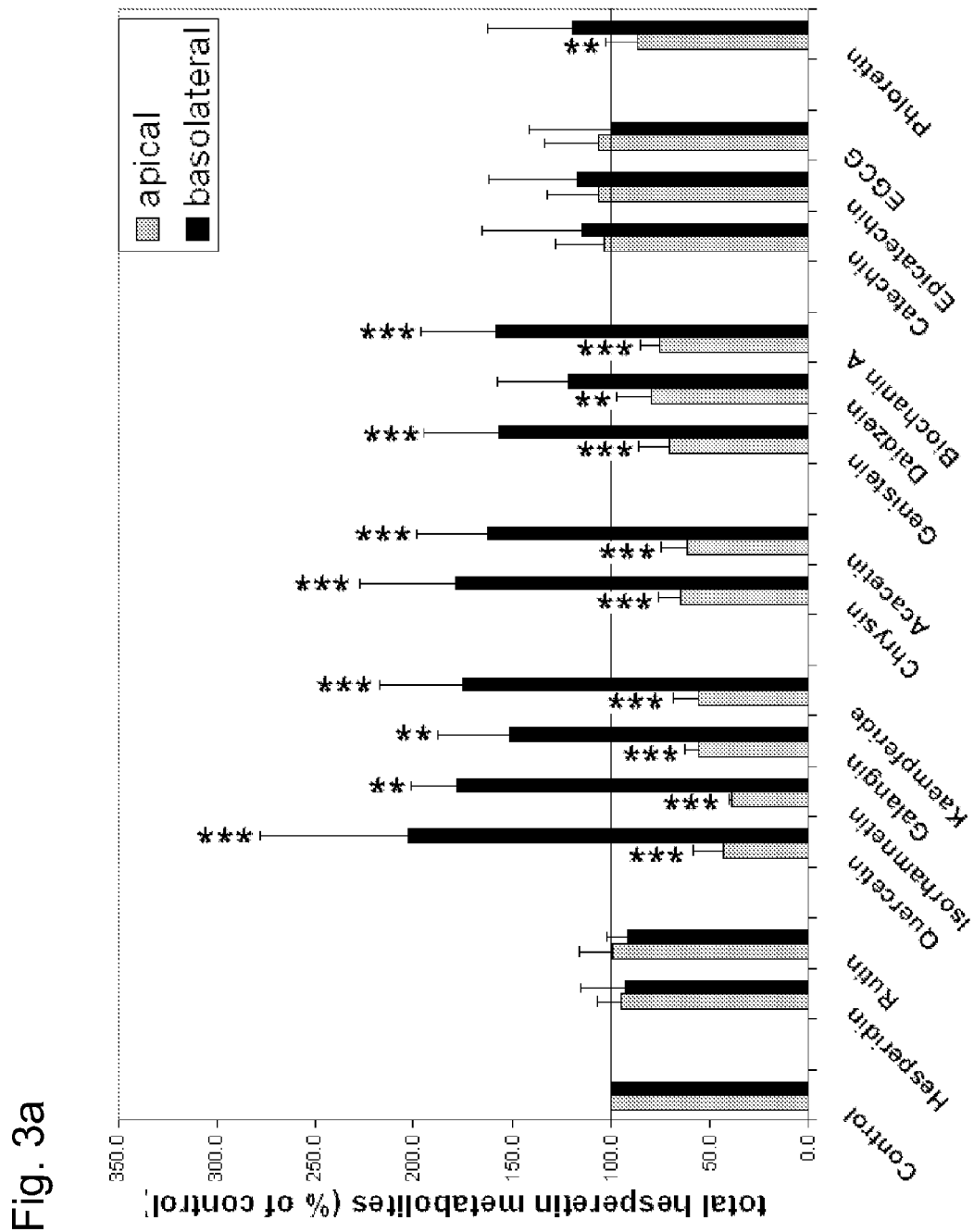
FIG. 3a shows the effect of different flavonoids (10 μM) on the apical and basolateral efflux of the sum of hesperetin 7-O-glucuronide and hesperetin 7-O-sulfate metabolites.
Figure 3B:
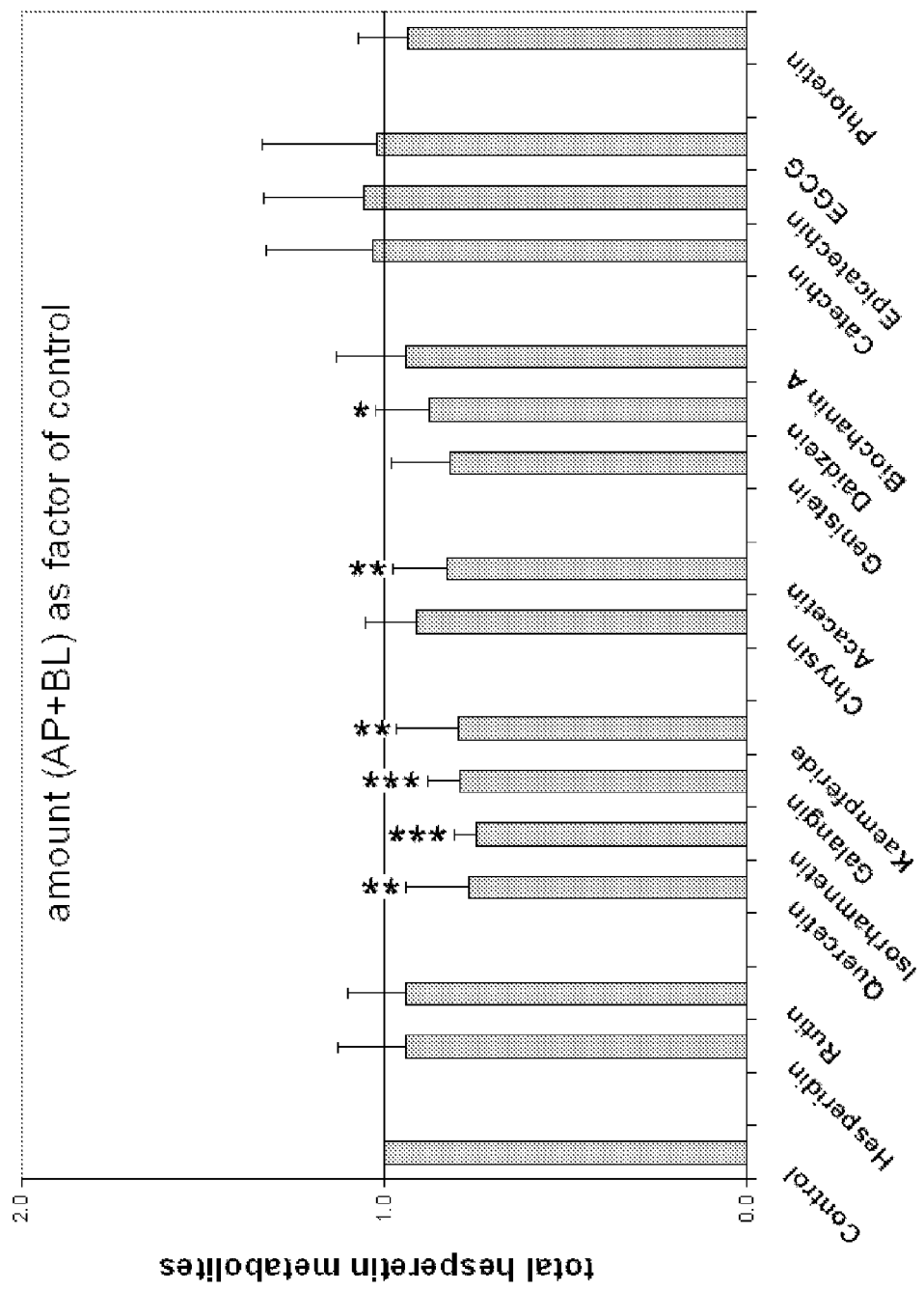

FIG. 3b shows the effect of different flavonoids (10 μM) on the sum of hesperetin 7-O-glucuronide and hesperetin 7-O-sulfate metabolites formed in the Caco-2 cell transwell model system, 120 minutes after being exposed at the apical side to 10 μM hesperetin in combination with the control of the corresponding experiment exposed only to 10 μM hesperetin (0.5% DMSO). Results are presented as mean±SD's. *=p<0.05, =p<0.01, *=P<0.001 significantly different from the control.

Figure 4:
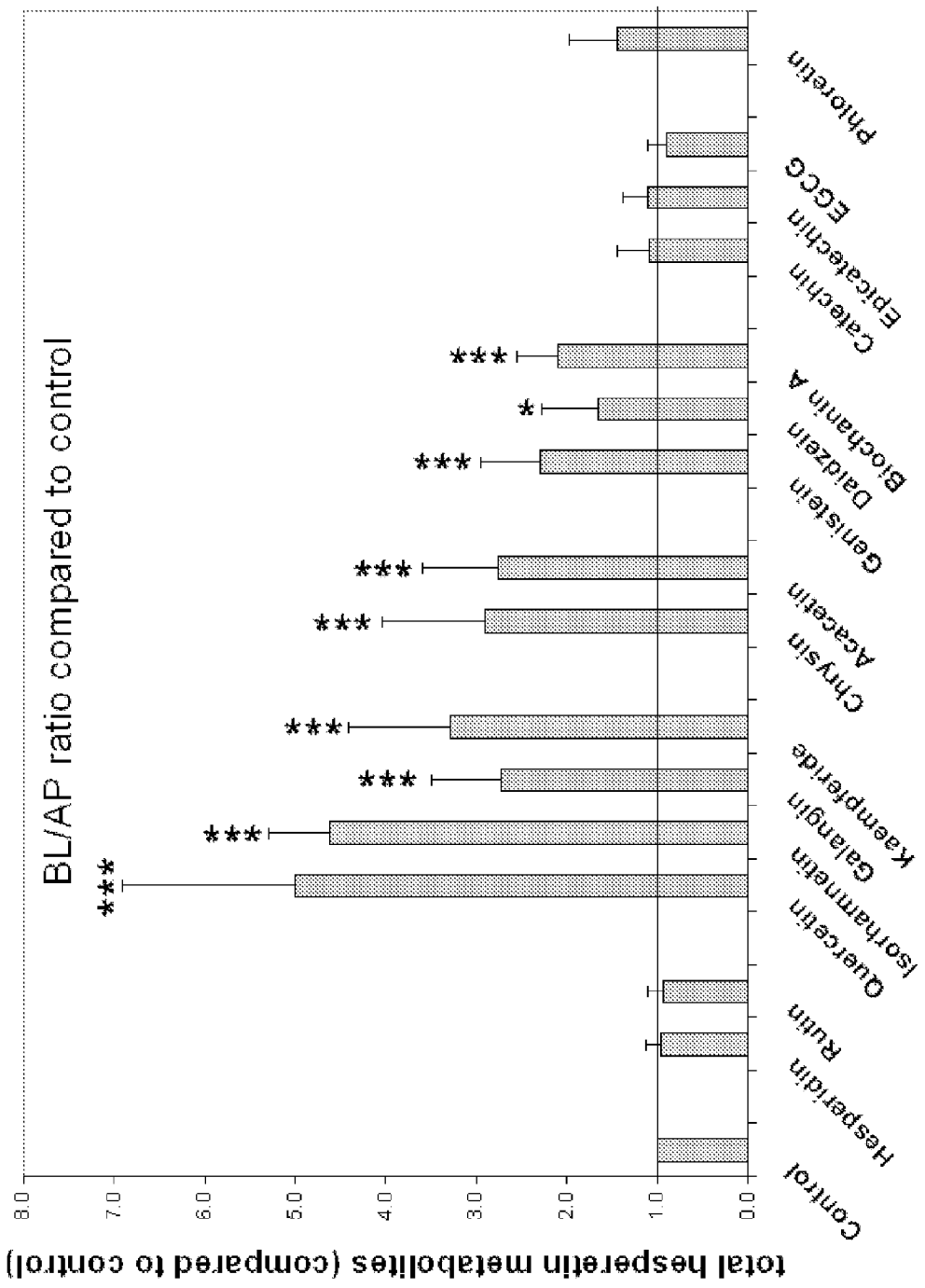

FIG. 4 shows the effect of different flavonoids (10 μM) on the ratio of basolateral and apical transported hesperetin metabolites formed in the Caco-2 cell transwell model system, 120 minutes after being exposed at the apical side to 10 μM hesperetin in combination with the control of the corresponding experiment exposed only to 10 μM hesperetin (0.5% DMSO). Results are presented as mean+SD's. *=p<0.05, =p<0.01, *=P<0.001 significantly different from the control

EXAMPLES

Caco-2 cell monolayers were grown on permeable filters that divide a two-compartment cell culture system. Although originally derived from a colonic adenoma carcinoma, differentiating Caco-2 cells are known to display morphological and biochemical properties of intestinal enterocytes including the formation of a polarized layer with expression of ABC transport proteins including Pgp, MRP1, MRP2 and BCRP and metabolizing enzymes.

Using the Caco-2 cell monolayer Transwell model in which the cells in the apical compartment were exposed to hesperetin, or combinations of hesperetin and other flavonoids, we studied the formation and transport of intestinal hesperetin conjugates, which were formed by the Caco-2 cells. 120 minutes upon exposure to 10 μM (5 nmol) hesperetin added to the apical compartment. Hesperetin could be detected at the basolateral side, as well as 2 metabolites, which were detected at much higher amounts in the apical compartment compared to the basolateral. These metabolites were identified as hesperetin 7-O-glucuronide and hesperetin 7-O-sulfate.

Flavonoids are known inhibitors of BCRP (Katayama et al., Cancer Chemother Pharmacol. 2007; 60(6):789-97, Zhang et al, Biochem Pharmacol. 2005; 70(4):627-639, Zhang et al., Drug Metab Dispos. 2005; 33(3):341-8, Zhang et al., Mol Pharmacol. 2004; 65(5):1208-16, Zhang et al., Pharm Res. 2004; 21(7):1263-73, Imai et al., Cancer Res. 2004; 64(12):4346-52, Ahmed-Belkacem et al., Cancer Res. 2005; 65(11):4852-60, Cooray et al., Biochem Biophys Res Commun. 2004; 317(1):269-36, Yoshikawa et al., J Exp Ther Oncol. 2004; 4(1):25-35, Wang & Morris, Drug Metab Dispos. 2007; 35(2):268-74, Henrich et al., J Biomol Screen. 2006; 11(2):176-83, documents incorporated herein by reference). These studies include mainly in vitro studies of the effect of flavonoids on intracellular accumulation of, or cellular resistance to, substrates of BCRP, including nitrofurantoin, topotecan, mitoxantrone and fluorescent pheophorbide A, in BCRP over-expressing cell lines compared to wild-type or BCRP negative cells.

Since BCRP is the main responsible ABC transporter for the efflux of hesperetin metabolites from our Caco-2 cell monolayers, we performed experiments in which we studied the effect of co-administering different flavonoids, known to be good BCRP inhibitors from literature, or known not to affect BCRP as co-administrated compounds. In spite of the reduction in metabolites transported out of the cell in some cases (FIG. 3b) the amount of hesperetin metabolites transported to the basolateral side was significantly increased. The results (FIG. 3-4) indicate that co-administration of specific flavonoids decreases the apical efflux of hesperetin metabolites, while increasing the transport of hesperetin metabolites to the basolateral side. This demonstrates that co-administration of hesperetin with other flavonoids increases the bioavailability of hesperetin in vitro in a model simulating the intestinal transport barrier, and therefore, this could be a strategy to improve the bioavailability of hesperetin in vivo.

The invention claimed is:

1. A method for treating skin inflammation by increasing basolateral intestinal transport of hesperetin ((S/R)-2,3-dihydro-5,7-dihydroxy-2-(3-hydroxy-4-methoxyphenyl)-4H-1-benzopyran-4-one) in a mammal having the skin inflammation comprising the step of administering a composition comprising at least one flavonoid compound that is not hesperetin to the mammal, thereby the skin inflammation is reduced.

2. The method in accordance with claim 1, wherein the flavonoid compound is selected from the group consisting of compounds with the following general formula,

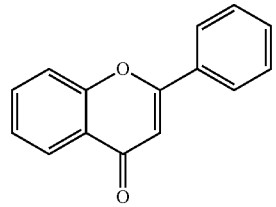

wherein carbons 3, 5, 6, 7, 8, 2', 3', 4', 5' and/or 6' are substituted equally or different from one another with an H, OH, or $OCH_3$ group, with the proviso that the compound is not hesperetin.

3. The method in accordance with claim 1, wherein at least one flavonoid compound is selected from the group consisting of quercetin, fisetin, chrysin, acacetin, apigenin, luteolin, tangeritin, baicalein, scutellarein, wogonin, diosmin and flavoxate, kaempferol, myricetin, fisetin, isorhamnetin, pachypodol, rhamnazin, hesperidin, rutin, galangin, kaempferide, genistein, daidzein, biochanin A, catechin, epicatechin, EGCG, phloretin, and combinations thereof.

4. The method in accordance with claim 1, wherein the compound is a dietary flavonoid.

5. The method in accordance with claim 1, wherein at least one flavonoid compound is present in the composition in an amount of 0.01 mg-10000 mg per daily dose.

6. The method in accordance with claim 1, wherein the composition comprises hesperetin, in an amount of 0.1 mg to 10000 mg.

7. The method in accordance with claim 1, wherein the flavonoid is hesperidin.

8. The method in accordance with claim 1, wherein the composition further comprises hesperetin that is provided in the form of an extract from herbs.

9. The method in accordance with claim 1, wherein the bioavailability of hesperetin is increased due to the increase in basolateral intestinal transport.

* * * * *